US010541977B2

(12) United States Patent
Wu et al.

(10) Patent No.: US 10,541,977 B2
(45) Date of Patent: Jan. 21, 2020

(54) UTILIZING SIGNED CREDENTIALS FOR SECURE COMMUNICATION WITH AN IMPLANTABLE MEDICAL DEVICE

(71) Applicant: Pacesetter, Inc., Sunnyvale, CA (US)

(72) Inventors: Yongjian Wu, Saratoga, CA (US); Mostafa Sadeghi, Los Angeles, CA (US); Chao-Wen Young, Cupertino, CA (US); Jun Yang, Valencia, CA (US); Samir Shah, Valencia, CA (US); Simon Skup, Santa Clarita, CA (US)

(73) Assignee: PACESETTER, INC., Sylmar, CA (US)

( * ) Notice: Subject to any disclaimer, the term of this patent is extended or adjusted under 35 U.S.C. 154(b) by 247 days.

(21) Appl. No.: 15/659,419

(22) Filed: Jul. 25, 2017

(65) Prior Publication Data

US 2019/0036886 A1   Jan. 31, 2019

(51) Int. Cl.
*H04L 29/06* (2006.01)
*A61N 1/372* (2006.01)
*A61B 5/00* (2006.01)

(52) U.S. Cl.
CPC ...... *H04L 63/0407* (2013.01); *A61N 1/37282* (2013.01); *A61B 5/0006* (2013.01); *A61B 5/0031* (2013.01); *H04L 63/0272* (2013.01); *H04L 63/0823* (2013.01)

(58) Field of Classification Search
CPC . H04L 63/08; H04L 63/0869; H04L 63/0876; H04L 63/105; H04L 63/12; H04L 63/126; H04L 9/32; H04L 9/321; H04L 9/3247; H04L 9/3263; H04L 9/3268; G06F 21/44; G06F 21/445; A61N 1/37254; A61B 5/0006; A61B 5/0031
See application file for complete search history.

(56) References Cited

U.S. PATENT DOCUMENTS

| 5,113,869 | A  | 5/1992  | Nappholz et al. |
| 5,313,953 | A  | 5/1994  | Yomtov et al. |
| 5,987,352 | A  | 11/1999 | Klein et al. |
| 6,496,715 | B1 | 12/2002 | Lee et al. |
| 7,027,858 | B2 | 4/2006  | Cao et al. |
| 8,391,960 | B2 | 3/2013  | Bornzin et al. |

(Continued)

FOREIGN PATENT DOCUMENTS

EP    3082356 A1    10/2016

OTHER PUBLICATIONS

Application filed Mar. 29, 2016; Related U.S. Appl. No. 15/084,373.

*Primary Examiner* — Eric W Shepperd
(74) *Attorney, Agent, or Firm* — Theresa A. Raymer (57) ABSTRACT

Methods and devices for establishing secure communications with an implantable medical device (IMD) are provided. The method and devices receive a credential from an external instrument (EI). The credential is signed utilizing a private key, and the credential includes at least two of a credential time to live (TTL) indicator, an IMD Identifier (ID), and an EI ID. The method and device authenticate the credential using a public key and verify the at least two of the TTL indicator, the IMD ID, and the EI ID. The method and device establish a secure communications session with the EI based on the verification and authentication.

24 Claims, 6 Drawing Sheets

(56) References Cited

U.S. PATENT DOCUMENTS

| | | | |
|---|---|---|---|
| 8,800,003 B2* | 8/2014 | Guo | H04L 63/0823 |
| | | | 726/4 |
| 8,831,747 B1 | 9/2014 | Min et al. | |
| 9,044,610 B2 | 6/2015 | Rosenberg et al. | |
| 9,215,075 B1* | 12/2015 | Poltorak | H04L 63/04 |
| 9,218,285 B2 | 12/2015 | Boling et al. | |
| 9,232,485 B2 | 1/2016 | Wu et al. | |
| 9,333,351 B2 | 5/2016 | Arnold et al. | |
| 9,463,325 B1 | 10/2016 | Young et al. | |
| 2001/0027331 A1* | 10/2001 | Thompson | A61N 1/37282 |
| | | | 607/60 |
| 2004/0185842 A1* | 9/2004 | Spaur | B60R 25/04 |
| | | | 455/420 |
| 2004/0260363 A1* | 12/2004 | Arx | A61N 1/37252 |
| | | | 607/60 |
| 2006/0030904 A1* | 2/2006 | Quiles | A61N 1/37252 |
| | | | 607/60 |
| 2008/0005573 A1* | 1/2008 | Morris | H04L 9/3257 |
| | | | 713/180 |
| 2009/0054948 A1 | 2/2009 | Webb | |
| 2009/0292340 A1* | 11/2009 | Mass | A61N 1/37282 |
| | | | 607/60 |
| 2010/0267418 A1* | 10/2010 | Toon | H04L 63/0853 |
| | | | 455/558 |
| 2011/0010543 A1* | 1/2011 | Schmidt | H04W 12/10 |
| | | | 713/168 |
| 2011/0319056 A1* | 12/2011 | Toy | H04L 9/3226 |
| | | | 455/412.2 |
| 2012/0166796 A1* | 6/2012 | Metke | H04L 9/321 |
| | | | 713/158 |
| 2013/0185783 A1* | 7/2013 | Jelatis | A61N 1/37252 |
| | | | 726/7 |
| 2013/0326596 A1* | 12/2013 | Hohlfeld | G06F 21/6218 |
| | | | 726/5 |
| 2014/0013109 A1* | 1/2014 | Yin | H04W 12/0608 |
| | | | 713/156 |
| 2015/0012990 A1* | 1/2015 | Copsey | H04L 63/0815 |
| | | | 726/7 |
| 2015/0073507 A1 | 3/2015 | Reinke et al. | |
| 2015/0134968 A1* | 5/2015 | Outwater | G06Q 30/06 |
| | | | 713/175 |
| 2016/0366183 A1* | 12/2016 | Smith | H04L 63/06 |
| 2017/0281032 A1 | 10/2017 | Weinberg et al. | |
| 2017/0374058 A1* | 12/2017 | Horiuchi | H04L 9/3263 |
| 2018/0243573 A1* | 8/2018 | Yoder | A61B 5/0031 |
| 2018/0295135 A1* | 10/2018 | Feijoo | H04L 63/10 |

\* cited by examiner

UTILIZING SIGNED CREDENTIALS FOR SECURE COMMUNICATION WITH AN IMPLANTABLE MEDICAL DEVICE

BACKGROUND

Embodiments of the present disclosure generally relate to systems and methods for establishing a secure communication with an implantable medical device based on signed credentials.

An implantable medical device (IMD) is a medical device that is configured to be implanted within a patient anatomy and commonly employs one or more electrodes that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external instrument as well as control patient therapy. The components of the IMD are hermetically sealed within a metal housing. The IMD is completely enclosed within the human body. Thus, there is no means of direct interaction with an IMD, other than through wireless communication.

However, IMDs are typically built with non-replaceable batteries that limit options for communications solutions. Typically, the wireless communication is maintained utilizing a low range, low power communications platform during short periods of time.

Existing communication solutions offer certain limitations. For example, in some environments, a challenge is presented for the IMD to authenticate an external instrument requesting to communicate there with. It is not practical for an authentication mechanism to base authentication on interaction with a user who enters information concerning the IMD into the external instrument. It is also not practical for the authentication mechanism to base authentication on communication with a remote secure server located at a remote location over a network. As one example, authentication methods that rely upon access to a remote server experience limits when network access is unavailable.

A need remains for improved methods and devices for establishing secure communication between IMDs and external instruments.

BRIEF SUMMARY

In accordance with embodiments herein, a method for establishing secure communications with an implantable medical device (IMD) is provided. The method comprises receiving a credential from an external instrument (EI), the credential signed utilizing a private key, the credential including at least two of a credential time to live (TTL) indicator, an IMD Identifier (ID), and an EI ID. The method further comprises authenticating the credential using a public key; verifying the at least two of the TTL indicator, the IMD ID, and the EI ID; and establishing a secure communications session with the EI based on the verifying and authenticating.

Alternatively, the method may include a verifying operation that may verifying that the TTL indicator, the IMD ID, and the EI ID are valid. The TTL indicator may be indicative of a period of time for which the credential remains valid, the verifying operation including comparing the TTL indicator with a current time maintained by the IMD to determine whether the TTL indicator has expired. The verifying operation may include confirming that the credential is addressed to the IMD by comparing the IMD ID from the credential with an ID stored in memory in the IMD.

Optionally, the method further comprising receiving a connection request prior to receiving the credential, the connection request including an EI ID, wherein the verifying operation includes confirming the credential is received from an authorized EI by comparing the EI ID from the credential and the EI ID from the connection request. The credential may include an access level, the method further comprising setting privileges for the secure communications session based on the access level from the credential. The private key may be maintained at a certification authority remote from the IMD and remote from the EI.

In accordance with embodiments herein, an implantable medical device (IMD) is provided. The IMD is comprised of a transceiver configured to receiving a credential from an external instrument (EI), the credential signed utilizing a private key, the credential including at least two of a time to live (TTL) indicator, an IMD Identifier (ID), and an EI ID. The IMD is further comprised of memory to store program instructions, a public key and an IMD ID uniquely associated with the IMD and a processor configured to execute the program instructions. The IMD further includes at least one of a circuit or the processor configured to authenticate the credential using the public key. The processor is further configured verify the at least two of the TTL indicator, the IMD ID, and the EI ID; and establish a secure communications session with the EI based on the verifying and authenticating.

Optionally, the IMD may further be comprised of a clock maintaining a current time, where the TTL indicator is indicative of a period of time for which the credential remains valid, the processor configured to perform the verifying operation by comparing the TTL indicator with the current time maintained by the clock of the IMD to determine whether the TTL indicator has expired. The processor may be configured to perform the verifying operation by confirming that the credential is addressed to the IMD by comparing the IMD ID from the credential with an ID stored in memory in the IMD. The transceiver may be configured to receive a connection request prior to receiving the credential, the connection request including an EI ID, wherein the processor is configured to perform the verifying operation by confirming the credential is received from an authorized EI by comparing the EI ID from the credential and the EI ID from the connection request. The credential may include an access level, and the processor may be configured to set privileges for the secure communications session based on the access level from the credential.

Additionally or alternatively, the IMD may further be comprised of an RF circuit that includes the processor, circuit, memory and transceiver; and a main controller circuit configured to manage at least one of sensing operations and therapy delivery operations, the main controller circuit separate from the RF circuit.

Optionally, the processor on the RF circuit may implement an authentication module to perform the authenticating the credential using the public key. The RF circuit may include an authentication circuit.

In accordance with embodiments herein, a method for establishing secure communications with an external instrument (EI) is provided. The method comprises receiving a credential at the EI from a certification authority, the credential signed utilizing a private key, the credential including at least two of a time to live (TTL) indicator, an IMD Identifier (ID), and an EI ID. The method further comprises establishing a wireless non-secure connection between the EI and an implantable medical device (IMD); transmitting the credential to the IMD over the wireless non-secure connection; and establishing a secure communications session with the EI based on authentication of the credential and verification of the at least two of the TTL indicator, the IMD ID, and the EI ID.

Optionally, the EI ID in the credential may correspond to a unique identifier for the EI receiving the credential and transmitting the credential to the IMD. The method may further comprise performing a registration operation with the certification authority, and receiving the credential from the certification authority in connection with the registration operation.

In accordance with embodiments herein, an external instrument is provided, comprised of memory to store program instructions and an EI identifier (ID) uniquely identifying the external instrument and a transceiver configured to communicate with an implantable medical device (IMD). The external instrument is further comprised of a communications interface configured to receive a credential from a certification authority, the credential signed utilizing a private key maintained at the certification authority, the credential including at least two of a time to live (TTL) indicator, an IMD Identifier (ID), and an EI ID. The external instrument includes a processor that, when executing the program instructions, is configured to establish a wireless non-secure connection between the EI and the IMD; transmit the credential to the IMD over the wireless non-secure connection; and establish a secure communications session with the EI based on authentication of the credential and verification of the at least two of the TTL indicator, the IMD ID, and the EI ID.

Optionally, the external instrument may have a transceiver configured to transmit a connection request to the IMD, the connection request including a connection EI ID associated with the external instrument, wherein the credential includes a credential EI ID to be compared, at the IMD, to the connection EI ID as part of a verification operation.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

The terms "signature" and "signed" refer to generating a digital signature for a credential or other content. By way of example, a credential digital signature may employ asymmetric cryptography and may be generated by applying a hash function to the credential.

Figure 1:
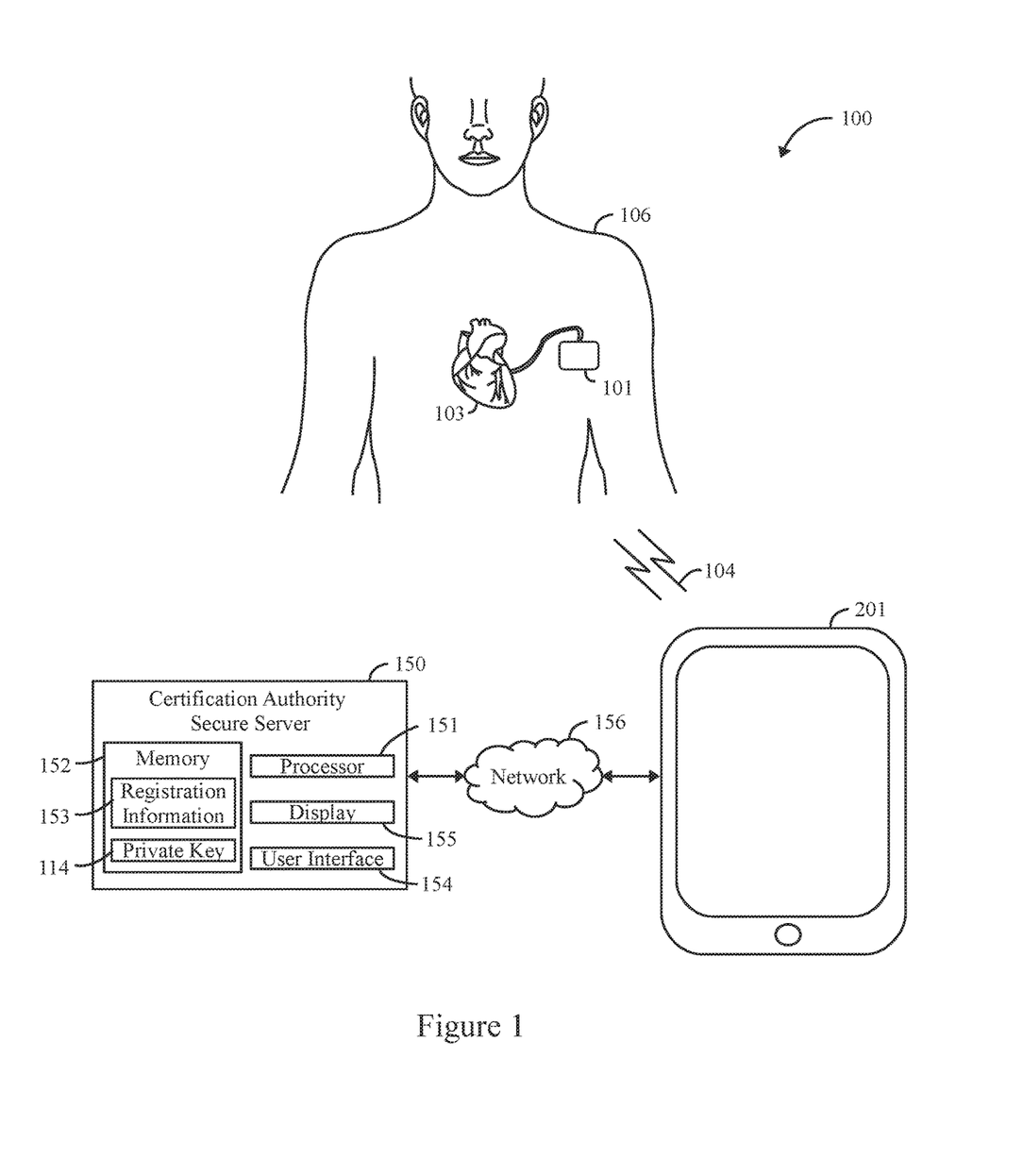
FIG. 1 illustrates a simplified block diagram of a system operated in accordance with embodiments herein.

FIG. 1 illustrates a simplified block diagram of a system 100 operated in accordance with embodiments herein. The system 100 includes one or more IMD 101 and one or more external instrument (EI) 201 (e.g., table computer, smart phone, smart watch, laptop, and/or the like) that are configured to communicate with one another wirelessly over a communications link 104. The system 100 also includes a certification authority 150 that is configured to communicate with the external instrument 201 over a network 156.

The IMD 101 is implanted within a patient 106 (e.g., proximate to and/or within a heart 103, proximate to the spinal cord). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. Additionally or alternatively, the IMD 101 may be a leadless monitor, examples of which are disclosed in U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

The certification authority 150 includes one or more processors 151, memory 152, a graphical user interface 154 and a display 155. The memory 152 stores instructions to manage operation of the processors 151. In addition, the memory 152 stores a private key 114 utilized for generating signed credentials. Optionally, the memory 152 may store registration information 153 in connection with IMDs and external instruments that are authorized for use with the certification authority 150. Optionally, the memory 152 may store multiple private keys 114 to be associated with different corresponding IMDs. As a further example, at the time each IMD is manufactured or implemented, a private-public key combination may be assigned to the IMD. The private key is stored at the certification authority and the public key is stored in the IMD.

The processors 151 typically includes a microprocessor, a micro-controller, or equivalent control circuitry, designed specifically to control interfacing with the EI 201 and with the IMD 101. The processors 151 performs the operations described herein by the certification authority 150 including but not limited to the registration process and generation and signature of credentials. For example, the processors 151 implement a signing algorithm that receives the private key 114 and the content of the credential and based thereon produces the signed credential. The graphical user interface 154 may include graphical icons, scroll bars, buttons, and the like which may receive or detect user or touch inputs 634 for the EI 201 when selections are made by the user.

Figure 2:
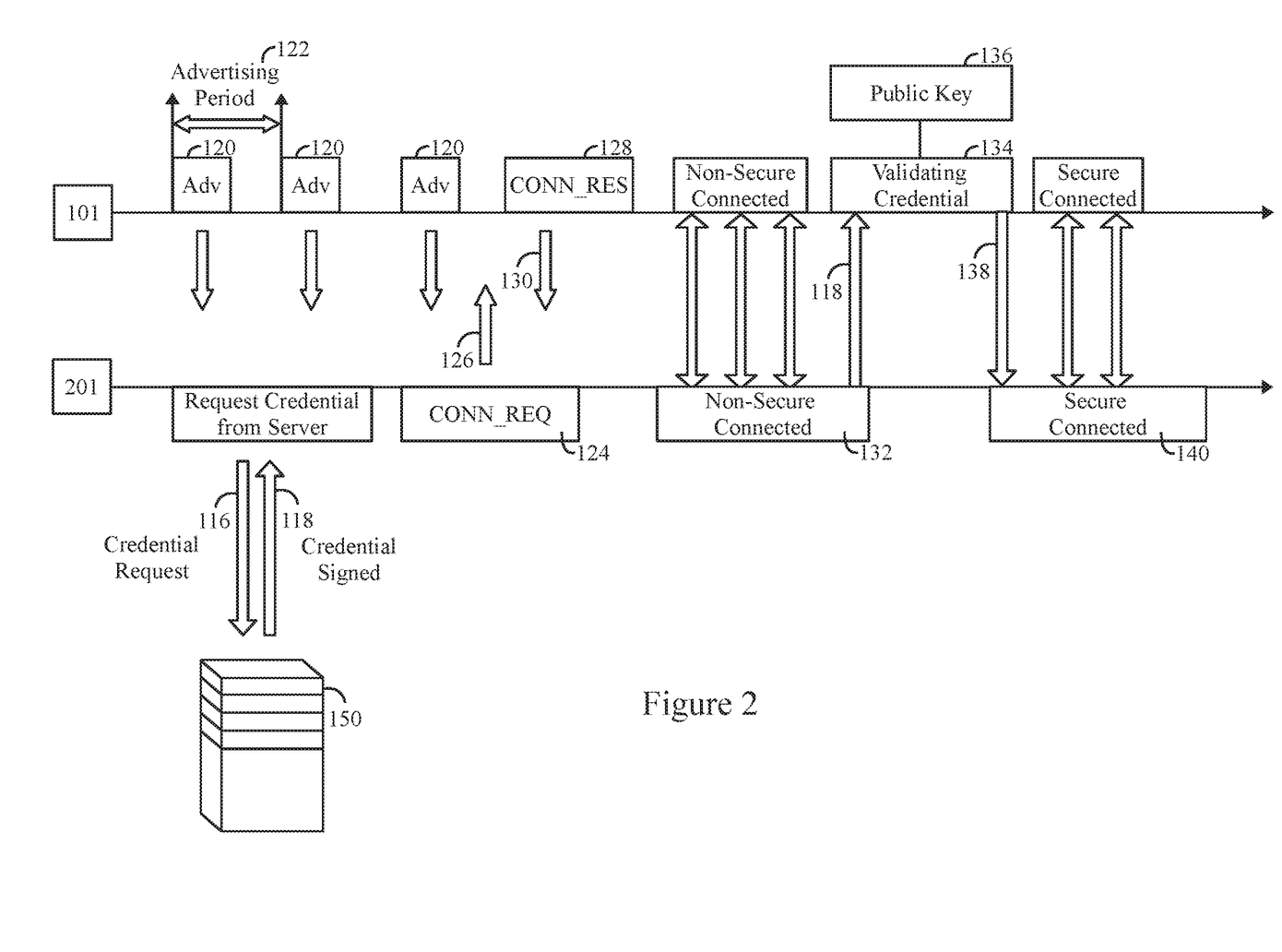
FIG. 2 illustrates a block diagram of communications exchanged between the IMD, external instrument and the certification authority implemented in accordance with embodiments herein.

FIG. 2 illustrates a block diagram of communications exchanged between the IMD 101, external instrument 201 and the certification authority 150 implemented in accordance with embodiments herein. It is understood that the order of operations may be varied and that various operations may be performed in parallel and/or merged into a common operation.

The external instrument 201 conveys a credential request 116 to the certification authority 150. The certification authority 150 validates the credential request 116 and based thereon, generates a signed credential 118 that is returned to the external instrument 201. The signed credential 118 is generated utilizing a private key 114 that is securely maintained at the certification authority 150.

The EI 201 is configured to establish a wireless bi-directional communication link 104 with the IMD 101. The communication link 104 allows the EI 201 to receive measurements from the IMD 101, and to program or send instructions to the IMD 101. The communication link 104 may use a standard wireless protocol such as Bluetooth Low Energy, Bluetooth, Medical Implant Communication Service, and/or the like. The EI 201 may be located within a home of the patient 106, a hospital, an automobile, at an office of the patient 106, or the like.

In accordance with at least some protocols, the IMD broadcasts advertisements 120 spaced apart by a predetermined advertising period 122. When the external instrument 201 is instructed to communicate with the IMD 101, the external instrument 201 initiates a connection request session 124, during which the external instrument 201 listens/scans one or more known channels for advertisements 120. When the external instrument 201 detects an advertisement 120, the external instrument 201 returns a connection request 126. The connection request includes an ID for the external instrument. The IMD 101 receives the connection request 126 and, during a connection response session 128, returns a connection response 130. The IMD 101 and external instrument 201 enter a non-secure communications session 132 during which non-secure information may be exchanged there between. The external instrument 201 transmits the signed credential 118 to the IMD 101 during the non-secure communications session 132, as part of a request to establish a secure communications link.

Embodiments herein provide an authentication mechanism that is based on verification of the credential 118, where the credential 118 is signed at the remote secure certification authority 150. The credential 118 is signed utilizing a private key (and optionally encrypted) at the certification authority 150. For example, the certification authority 150 may reside on a secure server that is maintained by a manufacturer of the IMD 101, a medical service provider, a hospital network and the like.

As explained herein, the IMD 101 performs a signature authentication and credential validation operations at 134. During signature authentication, the IMD 101 verifies the signature of the credential 118 utilizing a public key 136 and, based thereon, establishes a secure connection with the external instrument 201. The IMD 101 grants certain privileges to the external instrument 201 based on an access level designated within the credential 118. In accordance with embodiments herein, the credential 118 may contain various content that includes, among other things, a credential time to live (TTL) indicator, an IMD identifier (ID), an external instrument ID, and an access level. The credential 118 may include other content in addition to the content described herein. The TTL indicator defines an expiration date/time for the credential, after which the credential is no longer valid. The IMD ID uniquely defines the implantable medical device 101 for which the credential is valid. The IMD ID may be unique to a particular IMD 101 and/or unique to a select group of implantable medical devices. By embedding the IMD ID within the credential 118, embodiments herein prevent the credential 118 from being used with IMDs other than the specifically designated IMD 101 or group of IMDs.

The access level defines a set of privileges granted by the credential 118 for the external instrument 201. Different types of external instruments 201 may be afforded different privileges. For example, an external instrument 201 that represents a programmer utilized by a clinician, may be afforded greater privileges, as compared to the privileges afforded to a smart phone, home monitoring device, tablet device and the like utilized by a patient. The external instrument ID uniquely describes the external instrument 201 that is authorized to use the credential 118. By embedding the external instrument ID within the credential 118, embodiments herein enable the IMD 101 to determine which external instrument 201 is authorized to convey the credential to the IMD 101 in connection with requesting a secure communications session there between.

In accordance with embodiments herein, the IMD 101 authenticates the credential 118 utilizing the public key 136 that is maintained at the IMD 101. Once the IMD 101 authenticates the signature for the credential 118, the IMD 101 verifies the content of the credential 118 at 134. The verification operation at 134 includes confirming that the time to live indicator has not yet expired by the time that the external instrument 201 is attempting to establish the communication session. The verification operation at 134 includes comparing the credential IMD ID with the IMD ID stored within memory of the IMD 101 (e.g., stored at the time of manufacture or thereafter). The verification operation at 134 also compares the credential EI ID with an external instrument ID that the IMD 101 receives at the time that the external instrument initially requests the connection. When all or a predetermined number of the requisite verifications are confirmed, the IMD 101 transmits a secure connection acceptance message 138 to the external instrument 201. Thereafter, the IMD 101 and external instrument 201 establish a secure communications channel 140. Secure communication is supported through the secure communications channel 140 with the privileges associated with the access level within the credential 118.

In accordance with embodiments herein, at least one technical effect is that, by utilizes a public key 136 at the IMD 101 and including the credential content described herein, embodiments avoids the need to store a private key at the IMD. In the event that the public key 136 is compromised, an unauthorized entity would not be able to use the public key 136 to gain unauthorized access to the IMD 101 given that the public key is only capable of validating the credential 118 and is not capable of generating a credential. The unauthorized entity would not be able to create a signed credential with the credential content described herein. In accordance with embodiments herein, only the certification authority 150 maintains the private key 114 that enables the certification authority 150 to sign the credential 118. The private key 114 is never distributed and is maintained at a secure location at all times.

Figure 3:
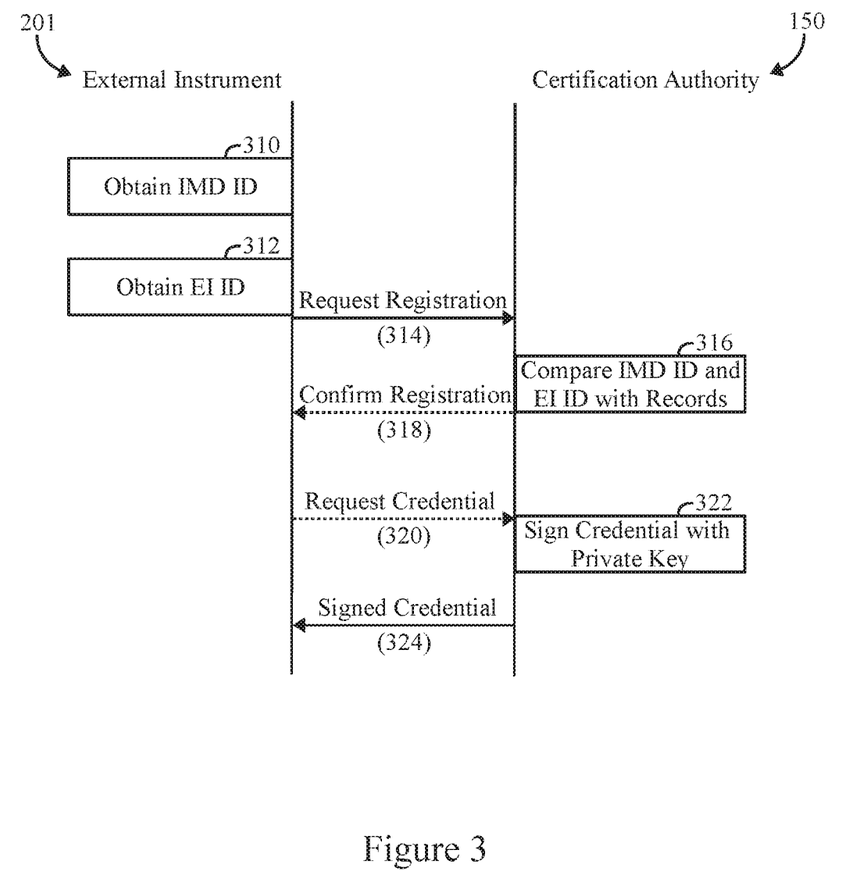
FIG. 3 illustrates a message sequence chart for a registration process between an external instrument and a certification authority implemented in accordance with embodiments herein.

FIG. 3 illustrates a message sequence chart for a registration process between an external instrument 201 and a certification authority 150 implemented in accordance with embodiments herein. It is understood that the order of operations may be varied and that various operations may be performed in parallel and/or merged into a common operation. The external instrument 201 obtains an IMD ID (at 310), which may represent a serial number or other identifier of the implantable medical device 101. The IMD ID may be unique to the particular implantable medical device 101 or common to a particular group of implantable medical devices. For example, the IMD ID may represent numeric or class identifier for a particular group of implantable medical devices. The IMD ID may be obtained in various manners. For example, the external instrument 201 may represent a programmer, in which case the clinician may enter the IMD ID. Optionally, the external instrument 201 may represent a patient's smart phone, tablet device or other home monitoring equipment utilized by the patient. External instruments 201 under the control of the patient may obtain an IMD ID in various manners. For example, the IMD ID may be uploaded to the external instrument automatically in connection with loading an application utilized with the IMD 101. Optionally, the patient may be provided with the IMD ID and allowed to enter the IMD ID into the external instrument 201 through a user interface thereof. Optionally, an initial pairing operation may be performed between the external instrument 201 and the IMD 101 (e.g., under control of the clinician) during which the external instrument 201 learns the IMD ID from the implantable medical device 101. Optionally, the external instrument 201 may receive the IMD ID from the certification authority 150 prior to the registration process of FIG. 3.

At 312, the external instrument 201 obtains a unique identifier associated with the external instrument 201. The external instrument ID may uniquely designate a physical device, an application operating on a particular physical device and/or an application operating on any physical device. The external instrument ID may represent a serial number or other unique identifier of the external instrument 201. For example, the serial number may correspond to the serial number of a smart phone, tablet device and the like. Additionally or alternatively, the external instrument ID may include in whole or in part a serial number or other unique identifier of an application operating on the external instrument 201 that enables the external instrument 201 to communicate with the IMD 101.

At 314, the external instrument 201 transmits a registration request to the certification authority 150. The registration request may be conveyed over the network 156 (FIG. 1). The registration request may include various information, such as the external instrument ID, the IMD ID and other registration related information. At 316, the certification authority 150 performs various registration related operations. The certification authority 150 may compare the received IMD ID with prerecorded records. For example, at the time of implant or thereafter, the certification authority 150 may store a patient record recording certain relevant information about the patient, as well as unique identifying information about the implantable medical device 101 within the patient. The registration request may include additional information about the patient (e.g. name, address, etc.) that is utilized to verify the registration request. When a match is identified, the certification authority 150 may determine that registration is appropriate.

Additionally or alternatively, the certification authority 150 may compare the external instrument ID, within the registration request, with prerecorded records. For example, home monitoring equipment (which represents one example of the external instrument 201) may be installed at a patient's home that is configured to communicate with the IMD 101. The home monitoring equipment may have a unique identifier that is stored with the certification authority 150 at the time that the home monitoring equipment is installed and set up. When the registration is authorized at the certification authority 150, the certification authority 150 returns a registration confirmation message (at 318). Thereafter, the external instrument 201 may convey a request for credentials (at 320) to the certification authority 150.

At 322, the certification authority 150 generates a credential that includes content of interest. As explained herein, the certification authority 150 generates a credential that includes i) a credential TTL indicator, ii) the IMD ID for which the credential is valid, iii) the EI ID that is authorized to utilize the credential and iv) an access level to be afforded to the user of the EI. For example, the certification authority 150 may set a credential TTL indicator to designate the credential to be valid for the next 24 hours, one week, one month, a set number of communication sessions or otherwise. The certification authority 150 signs the credential utilizing a private key maintained at the certification authority 150. Optionally, the certification authority 150 may also encrypt the signed credential. At 324, the signed credential is conveyed from the certification authority 150 to the external instrument 201.

The foregoing example describes a registration operation to be separate from the credential generation operation. Optionally, registration and credential generation operations may be combined and performed in parallel. For example, the external instrument 201 may convey the registration request (314) and credential request (320) in a common request, or at the same time as separate requests or otherwise. Similarly, the certification authority 150 may convey a registration confirmation (318) and a signed credential (324) as a common response, or at the same time as separate responses or otherwise. Optionally, the registration process may be omitted entirely, where only the operations of FIG. 3 concerning a request for credentials and a signed credential in response are performed. For example, the information collected in connection with registration may be entered at the certification authority separately from the external instrument (e.g., through a manual registration process).

Figure 4:
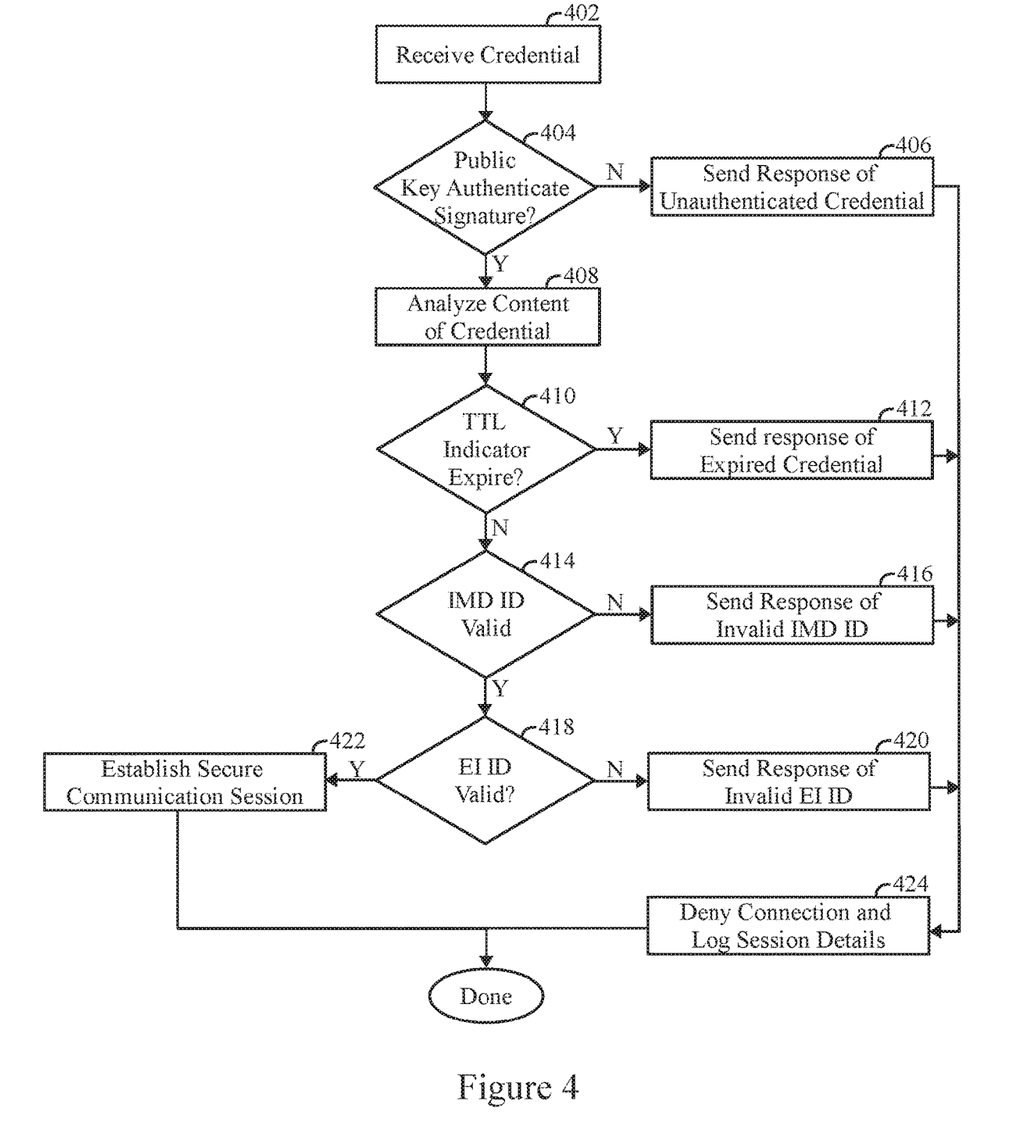
FIG. 4 illustrates a process for authenticating a signature and verifying a credential in accordance with an embodiment herein.

FIG. 4 illustrates a process for authenticating a signature and verifying a credential in accordance with an embodiment herein. The operations of FIG. 4 may be performed by the IMD 101, such as during the operations at 134 (FIG. 2). While the operations of FIG. 4 are described in a serial order, it is understood that the operations may be performed in parallel or in alternative orders.

At 402, IMD receives a signed credential during a non-secure connection session. At 404, one or more processors of the IMD utilize a public key stored within memory of the IMD 101 to attempt to authenticate the signature of the credential. Optionally, the IMD 101 may also decrypt the signed credential at 404, when the credential is encrypted. When the signature of the credential is not authenticated, flow moves to 406. At 406, the IMD sends a response to the external instrument 201 denying the connection and indicating the basis for denying the connection. For example, the IMD may send a response indicating that an unauthenticated credential was received. Optionally, at 406, the IMD may not send any response, but instead simply terminate the connection without explanation. For example, it may be preferable to not provide a basis for denying a connection, such as in order to avoid providing any unnecessary information to an unauthorized external instrument.

Flow moves from 406 to 424, where the connection is denied and the IMD stores a log of the session details. The log of the session details may include various information, such as the date and time of the session, identification information concerning the external instrument that is received during the connection process, the unauthenticated credential, and the like.

Returning to 404, when the signature of the credential is authenticated, flow moves to 408. At 408, the one or more processors of the IMD 101 analyze the content of the credential. At 410, the one or more processors determine whether the credential TTL indicator has already expired. When the TTL indicator has already expired, flow moves to 412.

At 412, the one or more processors of the IMD 101 send a response to the external instrument 201 indicating that the credential has expired. For example, it may be preferable in some instances to notify the external instrument 201 that a credential has expired, thereby affording the external instrument the opportunity to obtain a new credential from the certification authority. Optionally, the response indicating an expired credential may only be sent when other content of the credential has been verified. For example, when the IMD ID and EI ID within the credential are determined to be valid, but the TTL indicator has expired, the IMD 101 may determine that the external instrument 201 should be informed of the reason for denying the connection. The response would afford the external instrument 201 the opportunity to obtain a new credential. Alternatively, when the other content of the credential is not verified (e.g., the IMD ID and/or EI ID are not valid), the IMD 101 may determine that the external instrument 201 should not be informed of the reason for denying the connection.

Flow moves from 412 to 424 where the connection is denied and the IMD 101 stores a log of the session details. The log of the session details may include various information, such as the date and time of the session, any information concerning the external instrument 201 that is received during the connection process, the unverified credential and the like.

Returning to 410, when the TTL indicator has not yet expired, flow moves to 414. At 414, the one or more processors of the IMD 101 compare the IMD ID within the credential to a stored IMD ID within the implantable medical device 101. When the credential IMD ID and the stored IMD ID do not match, flow moves to 416. At 416, the one or more processors send a response to the external instrument 201 indicating that the IMD ID was in valid. For example, it may be preferable in some instances to notify the external instrument that the external instrument 201 is utilizing a credential directed to another IMD. For example, one patient may have multiple implantable devices where the patient uses the same external instrument to communicate with the multiple implantable devices. Notifying the external instrument that a credential directed to another IMD is utilized may be helpful to identify operational error occurs with the external instrument, certification authority and the like. Optionally, the response indicating an IMD ID mismatch may only be sent when other credentials have been verified.

Flow moves from 416 to 424 where the connection is denied and the IMD 101 stores a log of the session details. The log of the session details may include various information, such as the date and time of the session, any information concerning the external instrument that is received during the connection process, the unverified credential and the like.

Returning to 414, when the credential IMD ID and stored IMD ID match, flow moves to 418. At 418, the one or more processors of the IMD 101 compare the EI ID within the credential to an EI ID received from the external instrument 201 during the initial connection request (124 in FIG. 2). When the credential EI ID and the connection request EI ID do not match, flow moves to 420. At 420, the one or more processors send a response to the external instrument 201 indicating that the EI ID was invalid. For example, it may be preferable in some instances to notify the external instrument 201 that the external instrument 201 is utilizing a credential directed to another EI. For example, multiple external instruments may be utilized to access a common IMD 101. Notifying the external instrument 201 that a credential directed to another external instrument is utilized may be helpful to identify operational error occurs with the external instrument, certification authority and the like. Optionally, the response indicating an EI ID mismatch may only be sent when other credentials have been verified.

Flow moves from 420 to 424 where the connection is denied and the IMD 101 stores a log of the session details. The log of the session details may include various information, such as the date and time of the session, any information concerning the external instrument that is received during the connection process, the unverified credential, and the like.

Optionally, the operations at 406, 412, 416, 420 and 424 may be omitted entirely, such as when it is desirable to provide no reason for why a connection request is denied. Optionally, the operations at 406, 412, 416, 420 and 424 may be selectively performed. For example, the credential may include a relatively high access level, such as when a clinician is utilizing a programmer to communicate with the IMD. When the access level indicates that the external instrument represents a programmer, or other device used by a clinician or other authorized supervisory type individual, the IMD may provide the responses at 406, 412, 416, 420 and 424 to allow troubleshooting. Similarly, the credential may indicate a relatively low access level, such as afforded to a patient when obtaining basic information from the IMD. When a low access level is indicated within the credential, the IMD may determine to provide no or very limited information in a response when a connection is denied.

Returning to 418, when the credential EI ID matches an EI ID received during the connection request (also referred to as a connection request EI ID), the credential EI ID is validated, and in response thereto flow moves to 422. At 422, the IMD 101 and external instrument 201 exchange additional information warranted to establish a secure communications session there between. In connection with establishing the secure communications session, the one or more processors of the IMD 101 define the privileges to be afforded in connection with the communications session. The privileges are based on the access level designated within the credential.

In the foregoing example, a secure communications session is established only after validating the TTL indicator, credential IMD ID and credential EI ID. Optionally, a secure communication session may be established when at least a desired portion of the credential content is validated. For example, when two out of three of the TTL indicator, credential IMD ID and credential EI ID are valid, a secure communication session may be established. Optionally, an extent to which credential content mismatches may be considered. For example, when the TTL indicator expired only a few seconds or few minutes before the current communication session, a secure communication session may still be established if the remaining credential content (IMD ID and EI ID) are valid.

Figure 5:
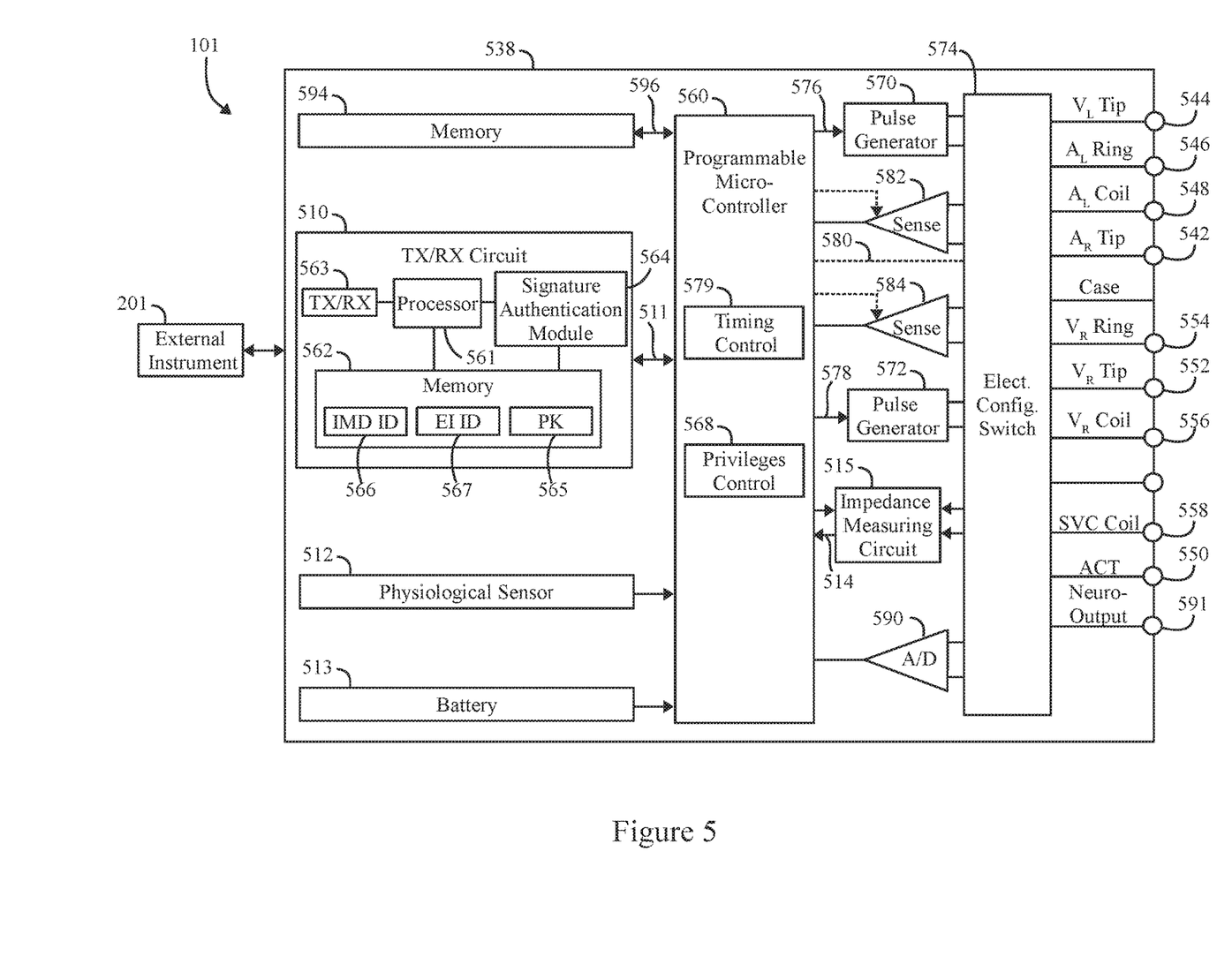
FIG. 5 illustrates a block diagram of internal components of the IMD.

FIG. 5 illustrates a block diagram of internal components of the IMD 101. The components described herein can include or represent hardware and software instructions (e.g., software stored on a tangible and non-transitory computer readable storage medium, such as a computer hard drive, read only memory (ROM), random access memory (RAM), or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

The IMD 101 is for illustration purposes only, and it is understood that the circuitry could be duplicated, eliminated or disabled in any desired combination to provide a device capable of treating the appropriate heart chamber(s) with cardioversion, defibrillation and/or pacing stimulation as well as providing for apnea detection and therapy. Additionally or alternatively, the IMD 101 may be used to generate neurostimulation for application to a desired area of a body, such as spinal cord stimulation, the brain and the like.

The housing 538 for the IMD 101, shown schematically in FIG. 2, is often referred to as the "can", "case" or "case electrode" and may be programmably selected to act as the return electrode for all "unipolar" modes. The housing 538 may further be used as a return electrode alone or in combination with one or more of the coil electrodes for shocking purposes. The housing 538 further includes a connector (not shown) having a plurality of terminals. The terminals may be configured to be coupled to different types of electrodes and leads. FIG. 2 illustrates various non-limiting examples of types/positions of electrodes that may be utilized. All or a portion of the terminals may be used in various combinations. It is recognized that alternative types of electrodes may be utilized in place of, or in addition to, the examples of FIG. 2. The following examples are provided as non-limiting examples of terminals: 542 (right atrial tip electrode), 544 (left ventricular tip electrode), 546 (left atrial ring electrode), 548 (left atrial coil electrode), 550 (acoustical terminal, ACT electrode), 552 (ventricular tip electrode), 554 (right ventricular ring electrode), 556 (right ventricular coil electrode), and 558 (superior vena cava coil electrode). In addition, a terminal 591 is indicated to be representative of one or more neural stimulation electrodes that may be utilized in place of or in addition to the above noted electrodes.

The IMD 101 includes a controller circuit 560 which controls operation of the IMD 101. The controller circuit 560 (also referred to herein as a processor module or unit) may include one or more processors, or equivalent control circuitry, designed specifically for controlling the delivery of stimulation therapy and may further include RAM or ROM memory, logic and timing circuitry, state machine circuitry, and I/O circuitry. Typically, the controller circuit 560 includes the ability to process or monitor input signals (data) as controlled by program code stored in memory. The details of the design and operation of the controller circuit 560 are not critical to the invention. Rather, any suitable controller circuit 560 may be used that carries out the functions described herein. Among other things, the controller circuit 560 receives, processes, and manages storage of digitized cardiac data sets from the various sensors and electrodes. For example, the cardiac data sets may include intracardiac electrogram (IEGM) data, pressure data, heart sound data, and the like.

The IMD 101 includes pulse generators 570, 572 to generate stimulation pulses for delivery by one or more leads and/or electrodes. The stimulation may be configured in different manners, such as in connection with neural stimulation, pacing pulse stimulation, cardioversion stimulation, defibrillation shocks, and the like The pulse generators, 570 and 572, may include dedicated, independent pulse generators, multiplexed pulse generators or shared pulse generators. The pulse generators, 570 and 572, are controlled by the controller circuit 560 via appropriate control signals, 576 and 578, respectively, to trigger or inhibit the stimulation pulses.

The pulse generators 570, 572 may be represent atrial and/or ventricular pulse generators, where the stimulation pulses are delivered through a plurality of electrodes and/or leads located within or proximate to the heart. Optionally, the pulse generators 570, 572 may represent neurostimulation pulse generators to generate stimulation pulses for a brain or spinal cord nervous system. The stimulation pulses are delivered by a plurality of electrodes through the neuro output lead 591. The neuro stimulation pulse generator circuit is controlled by the controller circuit 560 via appropriate control signals to trigger or generate the stimulation pulses.

The controller circuit 560 further includes timing control circuitry 579 used to control the timing of such stimulation pulses (e.g., the neural stimulation waveforms, pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. The controller circuit 560 also includes a privileges controller 568 that manages the privileges allowed in connection with a communication session based on the access level within the credential.

Switch 574 includes a plurality of switches for connecting the desired electrodes to the appropriate I/O circuits, thereby providing complete electrode programmability. Accordingly, the switch 574, in response to a control signal 580 from the controller circuit 560, determines the polarity of the stimulation pulses (e.g., unipolar, bipolar, etc.) by selectively closing the appropriate combination of switches (not shown).

A sensing circuit 582 and sensing circuit 584 may also be selectively coupled to one or more leads through the switch 574 for collecting sensed physiologic data (e.g. cardiac activity, neural activity, respiratory activity, etc.). The sensing circuits, 582 and 584, may include dedicated sense amplifiers, multiplexed amplifiers or shared amplifiers. The outputs of the sensing circuits, 582 and 584, are connected to the controller circuit 560 which, in turn, receives the sensed data and is able to trigger or inhibit the pulse generators, 570 and 572, respectively, in a demand fashion in response to the absence or presence of activity of interest.

Sensed signals are also applied to the inputs of an analog-to-digital (A/D) data acquisition system 590. The data acquisition system 590 is configured to acquire IEGM signals, neural signals, and the like. The data acquisition system 590 converts the raw analog data into a digital signal, and stores the digital signals in memory 594 for later processing and/or RF transmission to the EI 201. The data acquisition system 590 is coupled to one or more leads through the switch 574 to sample signals across any combination of desired electrodes. The data acquisition system 590 may also be coupled, through switch 574, to one or more of the acoustic sensors. The data acquisition system 590 acquires, performs A/D conversion, produces and saves the digital pressure data, and/or acoustic data.

The RF circuit 510 may be configured to handle and/or manage the bi-directional communication link between the IMD 101 and the EI 201. As explained herein, the RF circuit 510 transmits, among other things, advertising notices in accordance with one or more advertising schedules. The RF circuit 510 also scans for connection requests from the EI 201. The RF circuit 510 includes an RF control processor 561, the local memory 562, a transceiver 563 (TX/RX) and a signature authentication module 564, all of which may be implemented on a common circuit board, within a common subsystem or within a common integrated circuit. The transceiver 563 is tuned to communicate with the external instrument over one or more frequency bands and in accordance with a corresponding protocol.

The memory 562 stores instructions implemented by the RF control processor 561 to manage the credential signature authentication and credential content verification described herein, as well as other operations related to establishing and maintaining communication in accordance with the desire protocol. The memory 562 may store the public key 565 to be utilized in connection with establishing secure communications with the IMD. The memory 562 may also store the IMD ID 566 that is assigned at the time of manufacture or program at a later time therein. The memory 562 may also store the EI ID 567 that is received during each connection request.

The RF control processor 561 may support one or more wireless communication protocols while communicating with the EI 201, such as Bluetooth low energy, Bluetooth, Medical Implant Communication Service (MICS), and/or the like. The transceiver 563 may include one or more transmitters, receivers, and/or transceivers. Optionally, the RF circuit 510 may be electrically coupled to an antenna (not shown). For example, an antenna may be provided within a header of an IMD as one example. As another example, electrodes on or coupled to the IMD may be utilized to convey the wireless communication signals. Protocol firmware may be stored in memory 562, which is accessed by the RF control processor 561. The protocol firmware provides the wireless protocol syntax for the RF control processor 561 to assemble data packets, advertisement notices, connection requests, connection responses, establish communication links 104, and/or partition data received from the EI 201.

The signature authentication module 564 may be implemented in a hard wired circuit, firmware circuitry or as software implemented by the RF control processor 561. The signature authentication module 564 applies the public key 565 to incoming credentials and based on the results, provides an authenticated or unauthenticated indication to the RF control processor 561. The RF control processor 561 manages nonsecure and secure connections with external instruments as described herein. Before converting a communication session from a nonsecure connection to a secure connection, the RF control processor 561 performs the verifications described herein, such as described in connection with the operations at 408-424 in FIG. 4. In accordance with embodiments herein, the RF control processor 561 is configured to execute program instructions from memory. The authentication operation may be performed by at least one of the RF control processor 561 and/or a circuit hardwired to perform signature authentication to authenticate incoming credentials using the public key 565. The RF control processor is further configured to perform the following verifying the at least two of the TTL indicator, the IMD ID, and the EI ID; and establishing a secure communications session with the EI based on the verifying and authenticating.

Optionally, the communications session may be managed by the controller circuit 560. For example, the controller circuit 560 may manage nonsecure and secure connections with external instruments, as well as perform all or a portion of the verifications described herein. For example, the memory 594 may store instructions implemented by the controller circuit 560 to manage the credential signature authentication and credential content verification described herein, as well as other operations related to establishing and maintaining communication in accordance with the desire protocol. The memory 594 may store software to implement the signature authentication module 564 at the controller circuit 560. The memory 594 may store the public key 565 to be utilized in connection with establishing secure communications with the IMD 101. The memory 594 may also store the IMD ID 566 that is assigned at the time of manufacture or program at a later time therein. The memory 594 may also store the EI ID 567 that is received during a connection request.

The controller circuit 560 is coupled to the memory 594 by a suitable data/address bus 596, wherein the programmable operating parameters used by the controller circuit 560 are stored and modified, as required, in order to customize the operation of IMD 101 to suit the needs of a particular patient. The memory 594 also stores data sets (raw data, summary data, histograms, etc.), such as the IEGM data, heart sound data, pressure data, mixed venous oxygen saturation (SvO2) data and the like for a desired period of time (e.g., 5 hour, 24 hours, 5 month). The memory 594 may store instructions to direct the controller circuit 560 to analyze the cardiac signals and heart sounds identify characteristics of interest and derive values for predetermined statistical parameters.

The pacing and other operating parameters of the IMD 101 may be non-invasively programmed into the memory 594 through the RF circuit 510 in bi-directional wireless communication with the EI 201. The RF circuit 510 is controlled by the controller circuit 560 and receives data for transmission over a control line 511. The RF circuit 510 allows intra-cardiac electrograms, pressure data, acoustic data, SvO2 data, and status information relating to the operation of IMD 101 (as contained in the controller circuit 560 or memory 594) to be sent to the EI 201 through an established bi-directional communication link 104. The RF circuit 510 also allows the EI 201 to program new pacing parameters and advertising schedules for the IMD 101.

To establish the communication link 104 between the EI 201 and the IMD 101, the controller circuit 560 may instruct the RF circuit 510 to transmit one or more advertisement notices on one or more advertisement channels corresponding to an advertising schedule stored in memory 594. The advertisement channel is a point to multipoint, unidirectional, channel to carry a repeating pattern of system information messages such as network identification, allowable RF channels to establish the communication link 104, and/or the like that is included within the advertisement notice. The advertisement notice may be repeatedly transmitted after a set duration or an advertisement interval based on an advertising schedule stored in the memory 594 until the communication link 104 is established with the EI 201.

The IMD 101 may also include a physiologic sensor 512, such as an accelerometer commonly referred to as a "rate-responsive" sensor because it is typically used to record the activity level of the patient or adjust pacing stimulation rate according to the exercise state of the patient. Optionally, the physiological sensor 512 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 512 may also be external to the IMD 101, yet still be implanted within or carried by the patient. A common type of rate responsive sensor is an activity sensor incorporating an accelerometer or a piezoelectric crystal, which is mounted within the housing 538 of the IMD 101.

Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 513, which provides operating power to all of the circuits shown. Optionally, the IMD 101 may include an impedance measuring circuit 515 which is enabled by the controller circuit 560 via a control signal 514. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 515 is advantageously coupled to the switch 574 so that impedance at any desired electrode may be will soon as the obtained.

Figure 6:
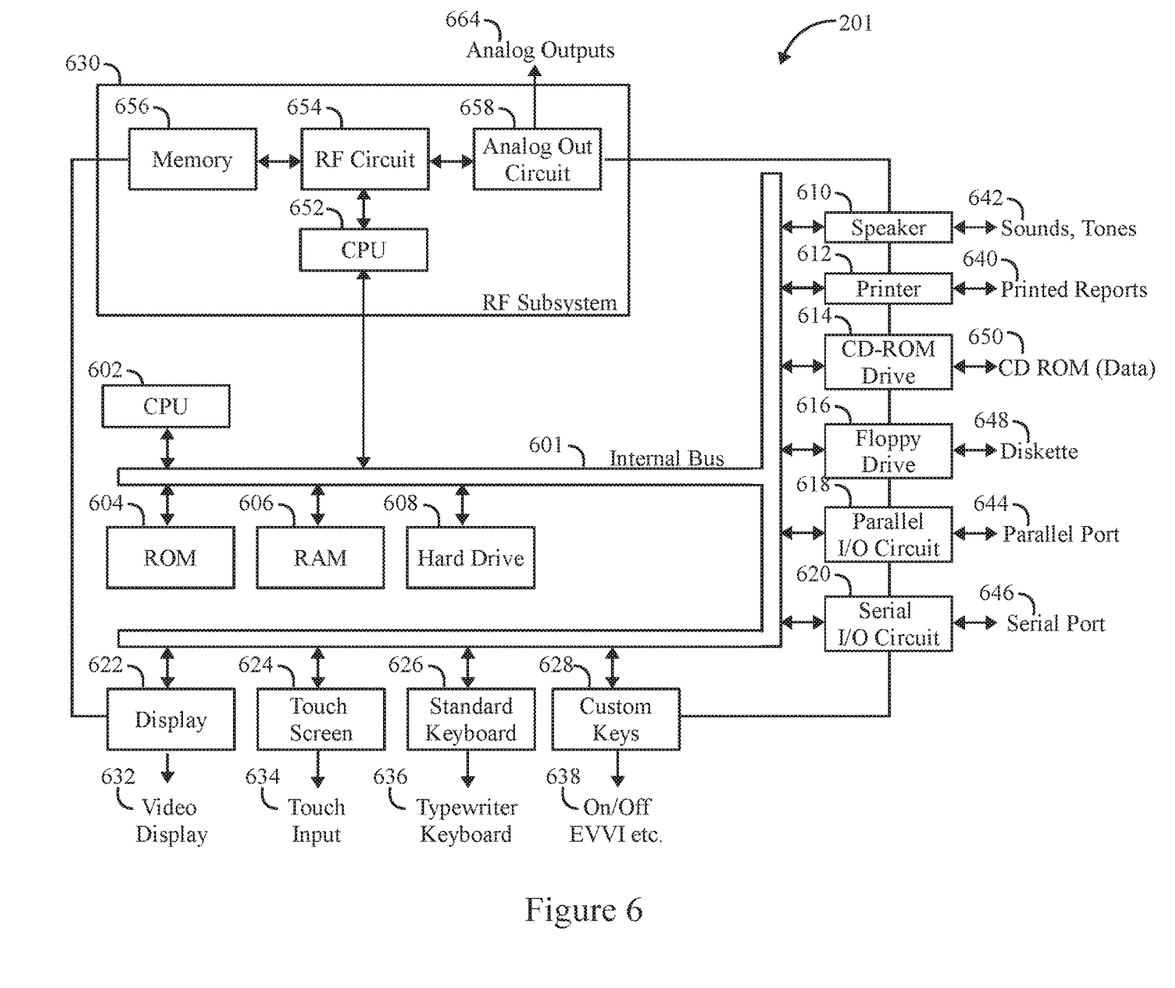
FIG. 6 illustrates a functional block diagram of the EI that is operated in accordance with embodiments herein.

FIG. 6 illustrates a functional block diagram of the EI 201 that is operated in accordance with embodiments herein. The EI 201 may be a workstation, a portable computer, a tablet computer, a smart watch, an IMD programmer, a PDA, a cell phone and/or the like. The EI 201 may include an internal bus 601 that may connect/interface with a Central Processing Unit ("CPU") 602, ROM 604, RAM 606, a hard drive 608, a speaker 610, a printer 612, a compact disc read only memory (CD-ROM) drive 614, a floppy drive 616, a parallel I/O circuit 618, a serial I/O circuit 620, the display 622, a touchscreen 624, a standard keyboard 626, custom keys 628, and an RF subsystem 630. The internal bus 601 is an address/data bus that transfers information between the various components described herein. The hard drive 608 may store operational programs as well as data, such as stimulation waveform templates and detection thresholds.

The CPU 602 typically includes a microprocessor, a micro-controller, or equivalent control circuitry, designed specifically to control interfacing with the EI 201 and with the IMD 101. The CPU 602 performs the operations described herein by the external instrument including but not limited to the registration process and operations for establishing a secure communications connection with an IMD. The CPU 602 may include RAM or ROM memory, logic and timing circuitry, state machine circuitry, and I/O circuitry to interface with the IMD 101. The display 622 (e.g., may be connected to the video display 632). The display 622 displays various information related to the processes described herein. The touchscreen 624 may display graphic information relating to the IMD 101 and include a graphical user interface. The graphical user interface may include graphical icons, scroll bars, buttons, and the like which may receive or detect user or touch inputs 634 for the EI 201 when selections are made by the user. Optionally the touchscreen 624 may be integrated with the display 622. The keyboard 626 (e.g., a typewriter keyboard 636) allows the user to enter data to the displayed fields, as well as interface with the RF subsystem 630. Furthermore, custom keys 628 turn on/off 638 the EI 201. The printer 612 prints copies of reports 640 for a physician to review or to be placed in a patient file, and the speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the serial I/O port may be coupled to a universal serial bus (USB) port or other interface capable of communicating with a USB device such as a memory stick. The CD-ROM drive 614 accepts CD ROMs 650. One or more scanning schedules are stored in the RAM 606, ROM 604, on a CD ROM 650, or elsewhere.

The RF subsystem 630 includes a central processing unit (CPU) 652 in electrical communication with an RF circuit 654, which may communicate with both the memory 656 and an analog out circuit 658. The analog out circuit 658 includes communication circuits to communicate with analog outputs 664. The EI 201 may wirelessly communicate with the IMD 101 and utilize protocols, such as Bluetooth, Bluetooth low energy, MICS, and/or the like. For example, the memory 656, ROM 604, and/or RAM 606 may include Protocol firmware, which is accessed by the CPU 652 and/or 602. The protocol firmware provides the wireless protocol syntax for the CPU 652 and/or 602 to assemble data packets, establish communication links 104, and/or partition data received from the IMD 101. The RF subsystem 630 and CPU 652 enter scanning states and establish communication sessions as described herein.

Closing Statement

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for establishing secure communications with an implantable medical device (IMD), the method comprising:
   receiving a credential from an external instrument (EI), the credential signed utilizing a private key, wherein the IMD and EI do not have access to the private key, the credential including an IMD identifier (ID) and at least one of a time to live (TTL) indicator or an EI ID;
   authenticating the credential using a public key;
   verifying the IMD ID and the at least one of the TTL indicator or the EI ID; and
   establishing a secure communications session with the EI based on the verifying and authenticating.

2. The method of claim 1, wherein the TTL indicator is indicative of a period of time for which the credential remains valid, the verifying operation including comparing the TTL indicator with a current time maintained by the IMD to determine whether the TTL indicator has expired.

3. The method of claim 1, wherein the verifying operation includes confirming that the credential is addressed to the IMD by comparing the IMD ID from the credential with an ID stored in memory in the IMD.

4. The method of claim 1, further comprising receiving a connection request prior to receiving the credential, the connection request including an EI ID, wherein the verifying operation includes confirming the credential is received from an authorized EI by comparing the EI ID from the credential and the EI ID from the connection request.

5. The method of claim 1, wherein the credential includes an access level, the method further comprising setting privileges for the secure communications session based on the access level from the credential.

6. The method of claim 1, further comprising assigning a private-public key combination that includes the public key utilized by the IMD and the private key utilized by the certification authority server, the private key stored in memory at the certification authority server with the EI having no access to the private key, the credential generated by one or more processors of the certification authority server utilizing the private key and including the IMD ID in the credential.

7. The method of claim 1, further comprising: providing the IMD ID from the IMD to the EI; convey a request for the credential from the EI to a certification authority server that maintains the private key, the request including the EI ID and the IMD ID; and generating the credential at the certification authority server utilizing the IMD ID, EI ID and private key.

8. An implantable medical device (IMD), comprising:
   a transceiver configured to receive a credential from an external instrument (EI), the credential signed utilizing a private key, wherein the IMD and EI do not have access to the private key, the credential including an IMD identifier (ID) and at least one of a time to live (TTL) indicator or an EI ID;
   memory to store program instructions, a public key and an IMD ID uniquely associated with the IMD;
   a processor configured to execute the program instructions;
   at least one of a circuit or the processor configured to authenticate the credential using the public key; and
   wherein the processor is further configured to perform the following:
   verifying the at least two of the TTL indicator, the IMD ID, and the EI ID; and
   establishing a secure communications session with the EI based on the verifying and authenticating.

9. The IMD of claim 8, further comprising a clock maintaining a current time, where the TTL indicator is indicative of a period of time for which the credential remains valid, the processor configured to perform the verifying operation by comparing the TTL indicator with the current time maintained by the clock of the IMD to determine whether the TTL indicator has expired.

10. The IMD of claim 8, wherein the transceiver is configured to receive a connection request prior to receiving the credential, the connection request including an EI ID, wherein the processor is configured to perform the verifying operation by confirming the credential is received from an authorized EI by comparing the EI ID from the credential and the EI ID from the connection request.

11. The IMD of claim 8, wherein the credential includes an access level, the processor is configured to set privileges for the secure communications session based on the access level from the credential.

12. The IMD of claim 8, further comprising:
   a radio frequency (RF) circuit that includes the processor, circuit, memory and transceiver; and
   a main controller circuit configured to manage at least one of sensing operations and therapy delivery operations, the main controller circuit separate from the RF circuit.

13. The IMD of claim 12, wherein the processor on the RF circuit implements an authentication module to perform the authenticating the credential using the public key.

14. The IMD of claim 12, wherein the RF circuit includes an authentication circuit.

15. The IMD of claim 8, wherein the private key and the public key are from a pre-assigning private-public key combination, the private key stored in memory at the certification authority server with the EI having no access to the private key, the credential generated by one or more processors of the certification authority utilizing the private key and including the IMD ID in the credential.

16. The IMD of claim 8, wherein the one or more processors are further configured to provide the IMD ID from the IMD to the EI, the EI to convey a request for the credential to a certification authority server that maintains the private key, the request including the EI ID and the IMD ID; and generating the credential at the certification authority server utilizing the IMD ID, EI ID and private key.

17. A method for establishing secure communications with an external instrument (EI), the method comprising:
   receiving a credential at the EI from a certification authority server, the credential signed utilizing a private key, wherein the IMD and EI do not have access to the private key, the credential including an IMD identifier (ID), and at least one of a time to live (TTL) indicator or an EI ID;
   establishing a wireless non-secure connection between the EI and an implantable medical device (IMD);
   transmitting the credential to the IMD over the wireless non-secure connection; and
   establishing a secure communications session with the EI based on authentication of the credential and verification of the at least two of the TTL indicator, the IMD ID, and the EI ID.

18. The method of claim 17, further comprising performing a registration operation with the certification authority server, and receiving the credential from the certification authority server in connection with the registration operation.

19. The method of claim 17, further comprising assigning a private-public key combination that includes the public key utilized by the IMD and the private key utilized by the certification authority, the private key stored in memory at the certification authority with the EI having no access to the private key, the credential generated by one or more processors of the certification authority utilizing the private key and including the IMD ID in the credential.

20. The method of claim 17, further comprising: providing the IMD ID from the IMD to the EI; convey a request for the credential from the EI to a certification authority server that maintains the private key, the request including the EI ID and the IMD ID; and generating the credential at the certification authority server utilizing the IMD ID, EI ID and private key.

21. A system, comprising:
an external instrument that comprises:
  memory to store program instructions and an EI identifier (ID) uniquely identifying the external instrument;
  a transceiver configured to communicate with an implantable medical device (IMD);
  a communications interface configured to receive a credential from a certification authority server, the credential signed utilizing a private key that is maintained at the certification authority server remote from the IMD and remote from the EI, wherein the IMD and EI do not have access to the private key, the credential including an IMD identifier (ID) and at least one of a time to live (TTL) indicator or an EI ID;
  a processor that, when executing the program instructions, is configured to perform the following:
    establishing a wireless non-secure connection between the EI and the IMD;
    transmitting the credential to the IMD over the wireless non-secure connection; and
    establishing a secure communications session with the EI based on authentication of the credential and verification of the at least two of the TTL indicator, the IMD ID, and the EI ID.

22. The system of claim 21, wherein the transceiver is configured to transmit a connection request to the IMD, the connection request including a connection EI ID associated with the external instrument, wherein the credential includes a credential EI ID to be compared, at the IMD, to the connection EI ID as part of a verification operation.

23. The system of claim 21, further comprising a certification authority server that includes memory and one or more processors, wherein the private key and the public key are from a pre-assigning private-public key combination that includes the public key utilized by the IMD and the private key stored and utilized by the certification authority server, the private key stored in memory at the certification authority server with the EI having no access to the private key, the credential generated by the one or more processors of the certification authority server utilizing the private key and including the IMD ID in the credential.

24. The system of claim 21, further comprising a certification authority server that includes:
memory configured to store the private key; and
one or more processors configured to:
  receive a request for the credential, the request including the EI ID and the IMD ID; and
  generate the credential utilizing the private key, the credential including the IMD ID, EI ID and the TTL indicator.

* * * * *